United States Patent [19]

Harris

[11] Patent Number: 4,567,901
[45] Date of Patent: Feb. 4, 1986

[54] PREBENT VENTRICULAR/ATRIAL CARDIAC PACING LEAD

[75] Inventor: Donald L. Harris, Key Largo, Fla.

[73] Assignee: Cordis Corporation, Miami, Fla.

[21] Appl. No.: 561,648

[22] Filed: Dec. 15, 1983

[51] Int. Cl.⁴ ............................................. A61N 1/05
[52] U.S. Cl. .................................. 128/786; 128/419 P
[58] Field of Search ............................... 128/784–786, 128/419 P, 642

[56] References Cited

U.S. PATENT DOCUMENTS

| | | | |
|---|---|---|---|
| 4,057,067 | 11/1977 | Lajos | 128/785 |
| 4,154,247 | 5/1979 | O'Neill | 128/419 P |
| 4,289,144 | 9/1981 | Gilman | 128/785 |
| 4,401,126 | 8/1983 | Reenstierna | 128/784 |

OTHER PUBLICATIONS

"The Porous-Surfaced Electrode", MacGregor et al, The Journal of Thoracic and Cardiovascular Surgery, St. Louis, vol. 78, No. 2, pp. 281–291, Aug., 1979.
"A Variation on the Introducer Technique for Unlimited Access to the Unlimited Access to the Subclavian Vein", Belott, PACE, vol. 4, pp. 43–48, Jan.–Feb., 1981.
"Routine Implantation of Permanent Transvenous Pacemaker Electrodes in both Chambers. A Technique Whose Time Has Come", Parsonnet, PACE, vol. 4, pp. 109–112, Jan.–Feb., 1981.
"Transvenous Physiological Pacing—A New Atrioventricular Electrode", PACE, vol. 5, pp. 264–267, Mar.–Apr., 1982, Llajos.

Primary Examiner—Lee S. Cohen
Attorney, Agent, or Firm—Lockwood, Alex, Fitzgibbon & Cummings

[57] ABSTRACT

A lead for effecting either or both of ventricular or atrial cardiac pacing is provided with a portion that is molded with a prebent condition which enhances the proper positioning of the atrial electrode and of the ventricular electrode within the heart, while also enhancing the maintenance of such leads at their respective implanted positions.

11 Claims, 5 Drawing Figures

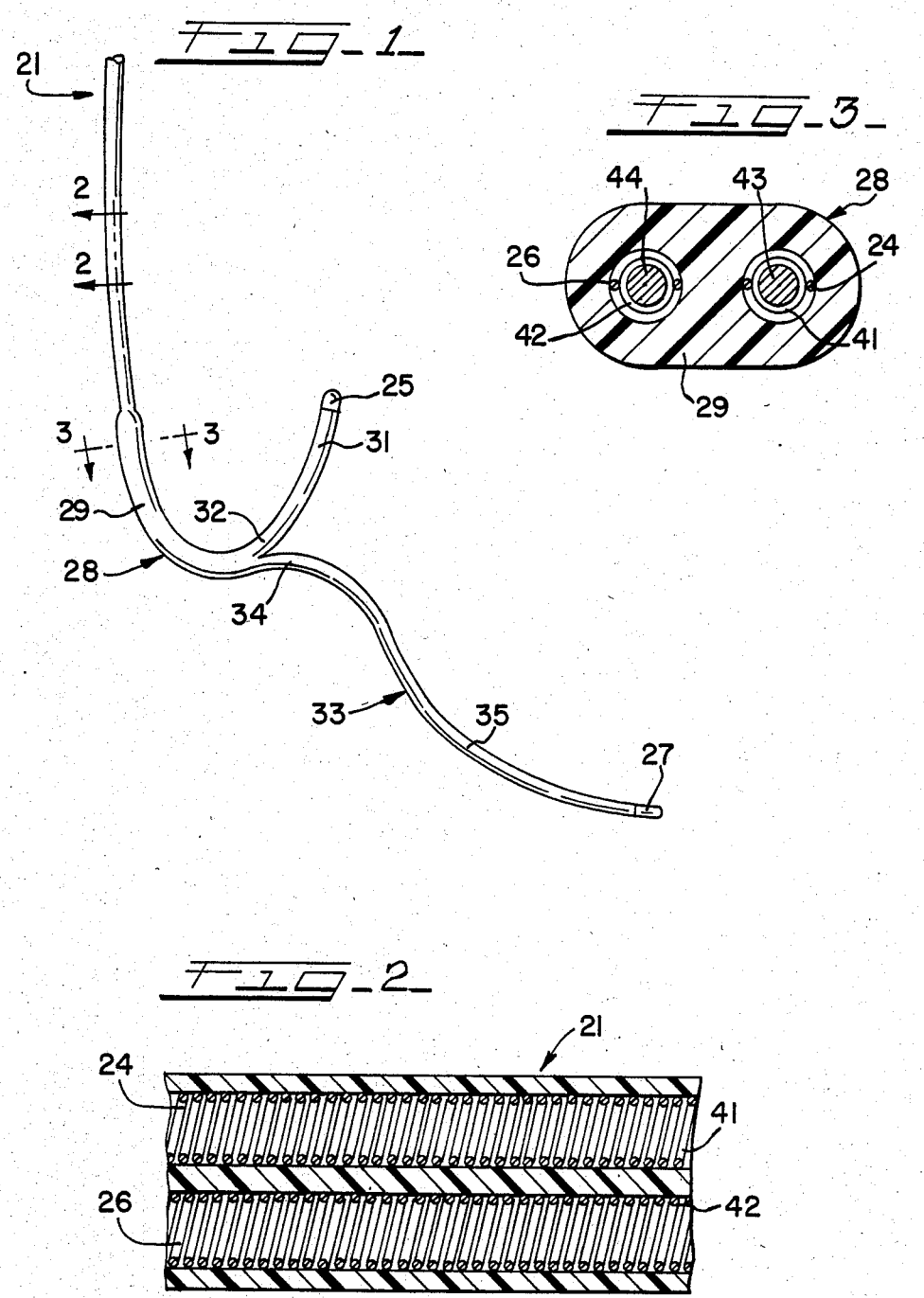

4,567,901

PREBENT VENTRICULAR/ATRIAL CARDIAC PACING LEAD

DESCRIPTION

BACKGROUND OF THE INVENTION

This invention generally relates to electrical leads for cardiac pacing, and more particularly to cardiac pacing leads that have both a ventricular lead and an atrial lead. The device includes a preshaped section that joins the atrial lead and the ventricular lead in a manner whereby the preshaped section urges both the atrial lead and the ventricular lead in their respective implanted positions.

There has recently been an increased interest in pacemaker leads that provide for dual-chamber pacing by which it is possible to carry on pacing in either or both of the atrium and/or the ventricle on the right side of the heart. In these instances, it is necessary to provide two separate and generally parallel elongated conductors that are implanted in substantially side-by-side relationship within a single vein such as a subclavian vein. In some implantation procedures, access is gained through a cephalic vein or external jugular vein. It is advantageous to avoid two separate incisions to provide access to the vein for both conductive and introducer devices, and pacer leads have been developed by which two electrodes can be inserted through the same vein, for example including the use of introducing sheaths that are inserted through a single incision and into the same vein.

Even with such improved techniques and devices, it is often difficult for the surgeon to accurately position the ventricular lead and the atrial lead at a location desired for implantation. These efforts can be further complicated when the atrial lead and the ventricular lead are tied together or slide over one another, to the extent that movement of one lead in an effort to properly position the same can detrimentally affect positioning of the other lead, requiring the surgeon to carry out a plurality of manipulative movements of the pacemaker lead in order to effect proper implantation.

SUMMARY OF THE INVENTION

By the present invention, it is possible to readily locate both the atrial lead and the ventricular lead, due in large measure to a specifically prebent or preshaped section including projections therefrom which are terminal, distal portions of the leads. This prebent or preshaped structure is such that, when implanted, the trunk portion thereof, the distal end of the atrial lead, and the distal end of the ventricular lead each impart a slight force onto an internal portion of the organ within which it is positioned. Each of said forces results in opposing forces that generally intersect in order to assist in stabilizing the maintenance of these three locations on the organ wall. The preshaped trunk portion of the prebent section is molded such that it has a non-linear, curved configuration, preferably having enhanced memory for its preshaped characteristics by virtue of its having a cross-section that is oversized with respect to other portions of the device. In addition, the prebent trunk portion has a distal end that bifurcates in oppositely bowed directions. One bow at the bifurcation is continuous with the curve of the trunk, this bow extending as the length of lead to which the atrial electrode is affixed. The other bow emanates from the bifurcation with a curve that is generally opposite to the curve of the trunk portion, this bow extending into and joining with the length of lead to which the ventricular electrode is affixed.

It is accordingly a general object of the present invention to provide an improved ventricular/atrial lead for a cardiac pacing device.

Another object of this invention is to provide an improved endocardial lead having a distal portion that is molded to have a prebent or preshaped condition so as to impart a plurality of generally opposing slight implantation forces to organ walls in order to enhance the securement of the lead in its pacing orientation.

Another object of this invention is to provide an improved cardiac lead for dual chamber pacing which utilizes a prebent or preshaped condition for providing generally opposing forces onto three different locations along the inner walls of the heart.

Another object of this invention is to provide an improved bifurcated pacing lead that imparts minimum column forces onto the implanted electrodes and into the tissue within which they are implanted.

Another object of the present invention is to provide an improved pervenous or transvenous bifurcated pacing lead having a distal portion that has a premolded shape that is generally curved and bifurcates into oppositely curved bows.

BRIEF DESCRIPTION OF THE DRAWING

These and other objects of the present invention will become apparent from the following detailed description thereof, taken in conjunction with the accompanying drawings, wherein:

FIG. 1 is an elevational view of the prebent or preshaped distal portion of a lead in accordance with this invention, shown in its molded, relaxed condition;

FIG. 2 is a longitudinal sectional view taken along the line 2—2 of FIG. 1;

FIG. 3 is a sectional view along the line 3—3 of FIG. 1;

DESCRIPTION OF THE PREFERRED EMBODIMENT(S)

Figure 5:
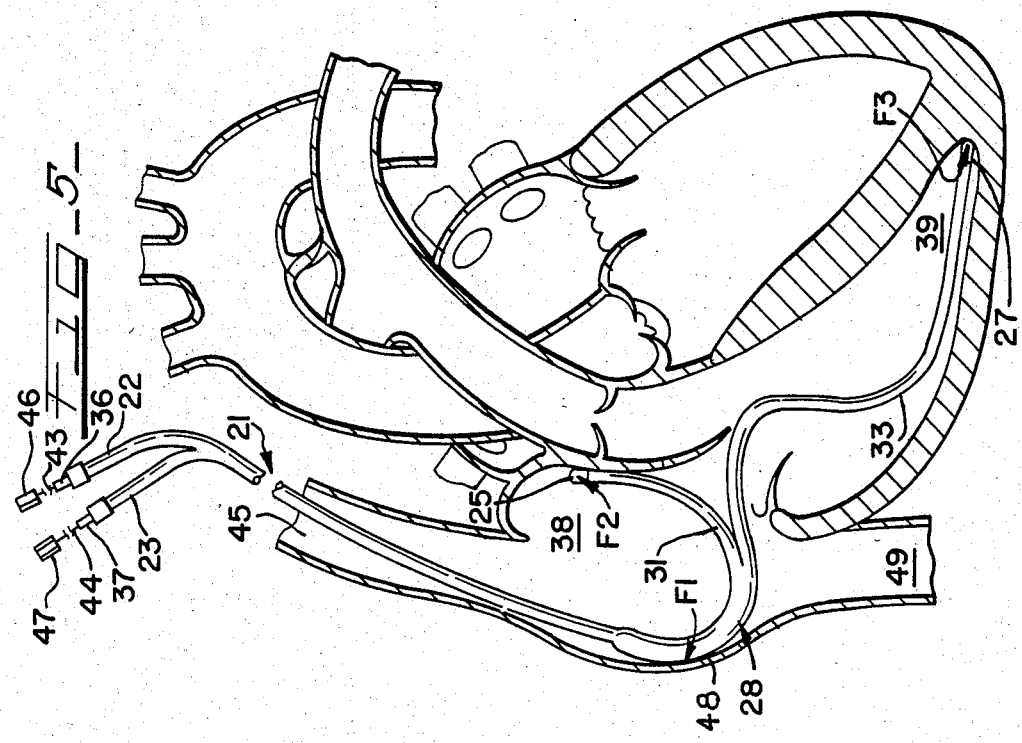
FIG. 5 is a view similar to FIG. 4, illustrating the lead as generally fully implanted.

The ventricular/atrial lead in accordance with this invention, generally designated as 21 in FIG. 5, includes an atrial lead portion 22 and a ventricular lead portion 23. The atrial lead portion 22 includes an atrial flexible electrical conductor 24 (FIG. 2) that extends generally through the lead 21 and terminates at an electrically conductive atrial electrode 25. The ventricular lead portion 23 includes a ventricular flexible electrode conductor 26 (FIG. 2) that extends generally through the lead 21 and terminates at an electrically conductive ventricular electrode 27.

A preshaped or prebent lead portion, generally designated as 28, is included near the distal end of the lead 21. Prebent portion 28 is molded such that, when same is in its relaxed condition as illustrated in FIG. 1, this prebent portion 28 includes a number of curved sections that interact with each other, and preferably are integrally molded with each other, in order to achieve the advantageous properties that are characteristic of this invention, which include same being disposed toward selfseating during and after implantation within a human heart.

These interacting curved sections of the prebent portion 28 include a trunk portion or primary curved section 29, which is generally continuous with and extends into an atrial curved section 31. The curvature of the atrial curved section 31 is continuous with the curvature of the primary curved section 29, these curvatures being in the same general direction to the extent that the primary curved section 29 and the atrial curved section 31 combine to form a generally J-shaped portion.

The preshaped or prebent portion 28 includes a bifurcation 32 which splits the prebent portion 28 into the atrial curved section 31 and into a ventricular curved section 33. Such ventricular curved section 33 includes a reversing curved section 34 which begins at and extends from the bifurcation 32. Preferably, the ventricular curved section 33 includes a re-reversing curved section 35 to the extent that the ventricular curved section 33 is generally S-shaped.

Prongs 36 and 37 extend from the respective proximal ends of the atrial lead 22 and of the ventricular lead 23. These prongs 36 and 37 are in operative electrical contact with the respective flexible electrical conductors 24 and 26, which in turn are in respective electrical contact with the electrodes 25 and 27. In accordance with conventional techniques, the prongs 36 and 37 are provided for electrically connecting the lead 21 to a suitable cardiac pacer device or pacemaker (not shown). With this arrangement, the pacemaker provides electrical stimulation within the atrium 38 and/or the ventricle 39 of a human heart in accordance with generally known procedures and techniques.

In this regard, it is important to accurately position the atrial electrode 25 and the ventricular electrode 27 and to maintain such position once it is initially established. While the atrial electrode 25 and ventricular electrode 27 may be of the self-attaching type, for example having a porous surface whereby ingrowth from the atrium 38 and the ventricle 39 serves to enhance holding of the electrodes 25 and 27, such ingrowth is somewhat gradual, and the electrodes 25 and 27 are susceptible of movement until adequate ingrowth has been established. The preshaped or prebent portion 28 is useful in this regard.

Atrial flexible electrical conductor 24 is located within an atrial lumen 41 that extends between the prong 36 and the atrial electrode 25. Ventricular flexible electrical conductor 26 is located within a ventricular lumen 42 which extends between the prong 37 and the ventricular electrode 27. Even with the respective electrical conductors 24 and 26 in place, the respective lumens 41 and 42 can accommodate respective stylets 43 and 44, typically made of spring wire.

In order to effect implantation of the ventricular/atrial lead in a typical surgical procedure, the lead is passed through a vein in order to gain access to the superior vena cava 45 for subsequent access to the right atrium 38 and to the right ventricle 39. Typically, the surgeon gains accesss to a suitable vein such as a subclavian, cephalic or external jugular vein by surgical incision at a suitable location. In many instances, access to the vein at the surgical incision is enhanced by an introducer sheath or the like (not shown) in accordance with known techniques. The lead 21 is then passed through the introducer sheath and through the vein which opens into the superior vena cava 45.

Figure 4:
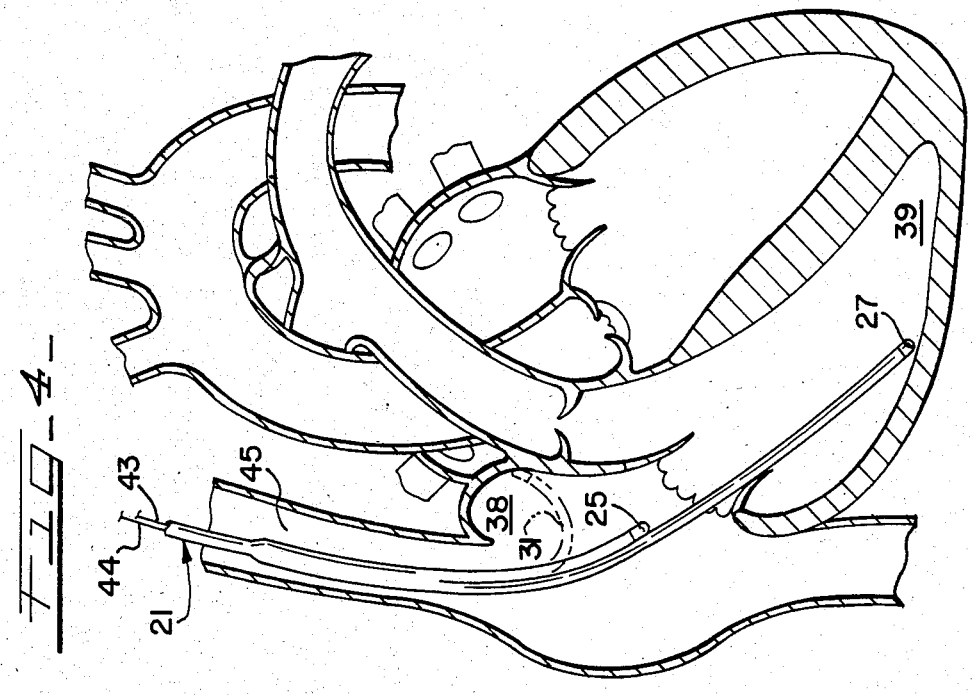
FIG. 4 is a drawing of a human heart illustrating the lead in accordance with this invention during an intermediate stage of its implantation.

During this passage through the vein, it is necessary to stiffen the lead 21 while also substantially straightening the preshaped or prebent portion 28. Such is accomplished by the insertion of either or both of the stylets 43, 44 into the respective lumens 41, 42. The lead 21 as illustrated in solid lines in FIG. 4 includes both stylets 43, 44 fully inserted to the electrodes 25 and 26, respectively. Use of the atrial stylet 43 could be omitted in at least some procedures by manually straightening the atrial curved section 31 and placing same into the introducer and then into the vein, provided the vein is able to maintain the general straightening of the atrial curved section 31 as the lead 21 passes therethrough. If the atrial stylet 43 is used, it is at least partially withdrawn by pulling on handle 46 until the atrial curved section 31 resumes its curvature and contacts a wall of the atrium 38, as shown in phantom in FIG. 4. If no atrial stylet 43 is used, then the memory of the atrial curved section 31 moves it to said position shown in phantom in FIG. 4 after the atrial electrode 25 exits with superior vena cava 45.

Next, with the ventricular stylet 44 still generally completely inserted into the lead 21, the surgeon continues with passage of the lead through the vein until the ventricular electrode 27 is well within the ventricle 39. At approximately the time that this insertion is taking place, the surgeon begins to withdraw the ventricular stylet 44 by pulling on the handle 47 until such time as the ventricular curved section 32 remanifests itself. This process continues until the ventricular stylet 44 (and the atrial stylet 43 if utilized) pass out of the preshaped or prebent portion 28.

At some point in time during this implantation procedure, the atrial electrode 25 contacts a wall of the atrium 38, the ventricular electrode 27 contacts a wall of the ventricle 39, and a generally convex outside portion of 48 of the primary curved section or trunk 29 contacts a surface generally between the superior vena cava 45 and the inferior vena cava 49, which is generally illustrated in FIG. 5. When this point in time is reached, the preshaped or prebent portion 28 assists in exerting forces in three different, generally opposing directions onto the wall between the superior vena cava 45 and the inferior vena cava 49, onto the wall of the atrium 38, and onto the wall of the ventricle 39. These forces are generally designated by arrows labeled as F1, F2 and F3, respectively, in FIG. 5.

With particular reference to the S-shape of the ventricular curved section 33 and the J-shape of the atrial curved section 31 such shapes are particularly advantageous for exerting an implantation maintenance force onto a wall of the ventricle 39 or the atrium 38, which force is adequate but does not create excessive column-type forces which would be imparted by the electrodes 25, 27 if the curved sections 31, 33 were relatively straight, rather than being curved as called for by this invention.

The ventricular atrial lead 21, and especially the preshaped or prebent portion 28 thereof, is molded of a body compatible material that is relatively strong yet somewhat pliable and soft. Preferred materials include polyurethane and silicone rubbers such as a Silastic material. Preferably, the prebent portion 28 is molded as a unit by injection molding techniques, often while previously extruded portions that project therefrom in the finished lead 21 are joined thereto by the same molding operation.

When the lead 21 is implanted as generally illustrated in FIG. 5, the atrial curved section 31 thereof is constantly urged by the wall of the atrium 38 in a direction generally opposing force F2, which tends to close up the J-shape of the prebent portion 28. For materials that tend to cold flow when subjected to human body temperatures for extended periods of time, which is the case for at least some polyurethanes, it can be desirable to optionally mold a length of flat spring wire into the atrial curved section 31 in order to minimize such cold flow effects.

Generally speaking, because the ventricular curved section 33 must be capable of more extensive bending than the atrial curved section 31, and also because the ventricular electrode 27 will generally engage the ventricle 39 in a substantially axial direction, the ventricular curved section 33 should be more flexible than the atrial curved section 31, which engages the atrium in a generally radial orientation and which is curved in a single general direction. This difference in flexibility can be achieved by molding the device such that the atrial curved section 31 has a cross-section that is generally thicker than the cross-sectional thickness of the ventricular curved section 33.

It will be apparent to those skilled in the art that various modifications are possible without departing from the spirit and scope of this invention; accordingly, this invention is to be construed only by the appended claims.

I claim:

1. A vertricular/atrial lead for a cardiac pacing assembly, comprising:
    an atrial lead having a flexible electrical conductor axially positioned therewithin, said atrial lead and flexible electrical conductor each having a proximal end and a distal end;
    a ventricular lead having a flexible electrical conductor axially positioned therewithin, said ventricular lead and flexible electrical conductor each having a proximal end and a distal end;
    an electrically conductive cardiac pacing atrial electrode in electrical and operative interengagement with said distal end of the atrial electrical conductor;
    an electrically conductive cardiac pacing ventricular electrode in electrical and operative interengagement with said distal end of the ventricular electrical conductor;
    a preshaped, prebent member positioned between said proximal ends and distal ends of the atrial and ventricular leads, said preshaped, prebent member being molded such that, when relaxed, it has a non-linear, curved shape; and
    said preshaped, prebent member includes a curved trunk portion having a distal end that bifurcates into generally oppositely curved portions, said atrial lead extending from one of said portions and said ventricular lead extending from another of said portions.

2. The lead as claimed in claim 1, wherein one of said generally oppositely curved portions is a curved atrial section onto which said atrial electrode is affixed, said curved trunk portion and said curved atrial section combining into a J-shape.

3. The lead as claimed in claim 1, wherein one of said generally oppositely curved portions is a generally S-shaped ventricular section onto which said ventricular electrode is affixed, said curved trunk portion and a proximal portion of said S-shaped ventricular section combining into an S-shape.

4. A ventricular/atrial lead for a cardiac pacing assembly, comprising:
    an atrial lead having a flexible electrical conductor axially positioned therewithin, said atrial lead and flexible electrical conductor each having a proximal end and a distal end;
    a ventricular lead having a flexible electrical conductor axially positioned therewithin, said ventricular lead and flexible electrical conductor each having a proximal end and a distal end;
    an electrically conductive cardiac pacing atrial electrode in electrical and operative interengagement with said distal end of the atrial electrical conductor;
    an electrically conductive cardiac pacing ventricular electrode in electrical and operative interengagement with said distal end of the ventricular electrical conductor;
    a preshaped, prebent member positioned between said proximal ends and distal ends of the atrial and ventricular leads, said preshaped, prebent member being molded such that, when relaxed, it has a non-linear, curved shape; and
    said preshaped, prebent member includes a curved trunk portion that is bifurcated at its distal end, said bifurcated distal end including a curved atrial section onto which said atrial electrode is affixed and a generally S-shaped ventricular section onto which said ventricular electrode is affixed.

5. The lead as claimed in claim 4, wherein said curved trunk portion has a cross-section that is oversized with respect to said curved atrial section and said generally S-shaped ventricular section.

6. The lead as claimed in claim 4, wherein said curved trunk portion has a cross-section that is oversized with respect to said curved atrial section and said generally S-shaped ventricular section, and said generally S-shaped ventricular section has a cross-section that is undersized with respect to said curved trunk portion and said curved atrial section.

7. The lead as claimed in claim 4, wherein said generally S-shaped ventricular section has a cross-section that is undersized with respect to said curved trunk portion.

8. The lead as claimed in claim 4, wherein said generally S-shaped ventricular section has a cross-section that is undersized with respect to said curved trunk portion and said curved atrial section.

9. The lead as claimed in claim 4, wherein said curved trunk portion bifurcation splits the preshaped, prebent member, said curved atrial section being generally continuous with the curvature of the curved trunk portion, and a proximal end of said generally S-shaped ventricular section being curved in a direction generally opposite to the curvature of the curved trunk portion.

10. The lead as claimed in claim 4, wherein said curved trunk portion has a generally convex outside portion, and wherein, when implanted within a human heart, each of said generally convex outside portion, said atrial electrode and said ventricular electrode impart respective forces in generally opposing directions.

11. The lead as claimed in claim 4, wherein said preshaped, prebent member is an integral mold and said bifurcated distal end of the curved trunk portion bifurcates in oppositely curved directions.

* * * * *

UNITED STATES PATENT AND TRADEMARK OFFICE
CERTIFICATE OF CORRECTION

PATENT NO. : 4,567,901
DATED : February 4, 1986
INVENTOR(S) : Donald L. Harris

It is certified that error appears in the above—identified patent and that said Letters Patent is hereby corrected as shown below:

Column 5, line 31, "vertricular/atrial" should read --ventricular/atrial--.

Signed and Sealed this

Twenty-ninth Day of July 1986

[SEAL]

Attest:

DONALD J. QUIGG

Attesting Officer

Commissioner of Patents and Trademarks